United States Patent [19]

Castagnola et al.

[11] Patent Number: 4,565,810

[45] Date of Patent: * Jan. 21, 1986

[54] DERIVATIVES OF BILIARY ACIDS, PROCESS FOR THE PRODUCTION THEREOF AND PHARMACEUTICAL COMPOSITIONS CONTAINING THE SAME

[75] Inventors: Virginio Castagnola, Milan; E. Giuliano Frigerio, Bresso; Roberto Pellicciari, Perugia, all of Italy

[73] Assignee: Lehner A.G., Muttenz, Switzerland

[*] Notice: The portion of the term of this patent subsequent to Apr. 30, 2002 has been disclaimed.

[21] Appl. No.: 603,332

[22] Filed: Apr. 24, 1984

[30] Foreign Application Priority Data

Apr. 29, 1983 [IT] Italy ................................ 20843 A/83

[51] Int. Cl.$^4$ .............................................. A61K 31/56
[52] U.S. Cl. .................................. 514/182; 260/397.1
[58] Field of Search ......................... 260/397.1, 397.2; 514/182

[56] References Cited

PUBLICATIONS

Chem. Abstract, vol. 100 (1984) Par. 210,254(v).

*Primary Examiner*—Elbert L. Roberts
*Attorney, Agent, or Firm*—Birch, Stewart, Kolasch & Birch

[57] ABSTRACT

New derivatives of chenodeoxycholic, ursodeoxycholic, cholic and ursocholic bile acids having in the side chain in the 19 position a cyclopropane ring are described together with taurine and glycine conjugated derivatives thereof.

The compounds of the invention, prepared from suitable olephinic intermediates by reaction with alkyl diazoacetates or by Simmons-Smith reaction and optional conjugation with taurine or glycine, are endowed with interesting therapeutic properties.

15 Claims, No Drawings

DERIVATIVES OF BILIARY ACIDS, PROCESS FOR THE PRODUCTION THEREOF AND PHARMACEUTICAL COMPOSITIONS CONTAINING THE SAME

This invention relates to a serie of novel biliary acids derivatives of formula (I)

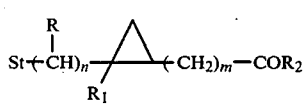

wherein: St represents the 17-ethiocholanyl residue, having two or more hydroxy groups both in the $\alpha$ and $\beta$ conformation, some of which being optionally replaced by keto groups;
n is zero or 1;
R and $R^1$ represent hydrogen or methyl, with the proviso that when one of them is methyl the other one is hydrogen;
m is zero, 1 or 2;
$R^2$ represents OH or taurine or glycine residues, optionally salified, of formula $-NH(CH_2)_2SO_3H$ and $NHCH_2COOH$;
with the proviso that when n is 1, m is zero and, when n is 1 and R is methyl, $R_2$ is different from OH.

The compounds of formula I present valuable pharmacological properties. The invention refers therefore also to pharmaceutical compositions containing as the active principle one or more compounds of formula (I) or their pharmaceutically acceptable salts.

Not limiting examples of compounds I of the present invention are the following ones:
sodium tauro-3$\alpha$,7$\beta$-dihydroxy-22,23-methanate-5$\beta$-cholanate (22,23-methanate-tauroursodesoxycholic acid) (n=1, R=CH$_3$, R$_1$=H, R$^2$=NH—CH$_2$-)$_2$—SO$_3$Na);
3$\alpha$,7$\alpha$,12$\alpha$-trihydroxy-21-nor-22,23-methanate-5$\beta$-cholanoic acid (n=1, R=R$_1$=H, R$^2$=OH);
3$\alpha$,7$\beta$,12$\alpha$-trihydroxy-20,21-bisnor-22,23-methanate-5$\beta$-cholanoic acid (n=0, R$_1$=H, m=0, R$^2$=OH);
tauro-3$\alpha$,7$\beta$-dihydroxy-20,21-bisnor-22-methyl-22,23-methanate-5$\beta$-cholanoic acid (n=m=0, R$_1$=CH$_3$, R$_2$=NH(CH$_2$)$_2$SO$_3$H);
sodium tauro-3$\alpha$,7$\alpha$-dihydroxy-20,21-bisnor-22,23-methanate-24-homo-5$\beta$-cholanate (n=0, R$_1$=H, m=1, R$_2$=NH(CH$_2$)$_2$—SO$_3$Na);
3$\alpha$-hydroxy-7-keto-20,21-bis-nor-22-methyl-22,23-methanate-24-homo-5$\beta$-cholanoic acid (n=0, R$_1$=CH$_3$, m=1, R$_2$=OH);
glyco-3$\alpha$,7$\beta$-dihydroxy-20,21-bis-nor-22,23-methanate-24,25-homo-5$\beta$-cholanoic acid (n=0, R$_1$=H, m=2, R$_2$=NH—CH$_2$—CO$_2$H).

The derivatives I conjugated with taurine or glycine (R$_2$ different from OH) are prepared from the corresponding acids (R$_2$=OH) by reaction with taurine or glycine in the presence of sodium hydroxide and N-ethoxycarbonyl-2-ethoxy-1,2-dihydroquinoline (EEDQ), in alcoholic or hydroalcoholic solution.

The compounds of formula I wherein R$_2$ is OH and m is 0 can be conveniently prepared by reaction of diazoacetates with suitable olephinic compounds III and subsequent ester hydrolysis.

In turn, the olephinic compounds III can be obtained by treating cholanic, nor-cholanic or bis-nor-cholanic acids II with lead tetraacetate (in the presence of Cu$^{++}$, preferably of rameic acetate) in pyridine.

Said process will be more evident from the scheme hereinafter reported for the sake of exemplification.

SCHEME I

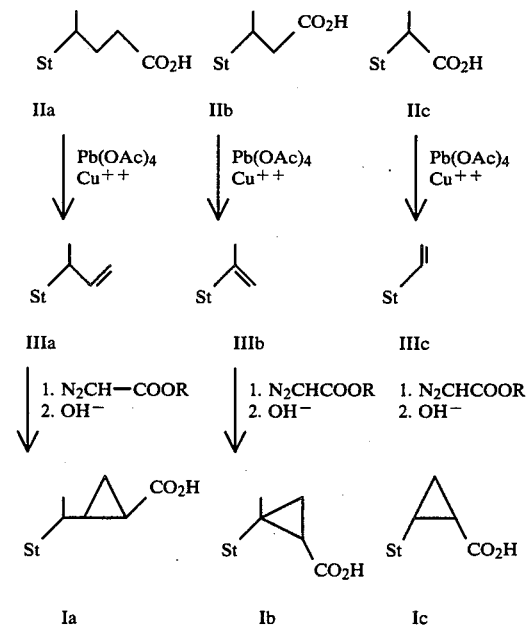

In the scheme I St has the above defined meaning, wherein however the hydroxy groups in $\alpha$ or $\beta$ position have been suitably protected, for instance transformed into the corresponding acetates by acetic anhydride.

As an example, the St group can therefore represent the following formula

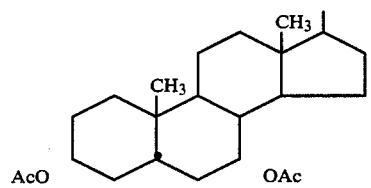

The compounds of general formula IIa, IIb or IIc are known. Compounds IIIb can also be obtained from cholic acids by a photochemical reaction in the presence of carbonyldiimidazole.

The other compounds of the invention can be obtained according to the following schemes wherein the St group, R$_1$ and m have the above defined meanings.

SCHEME II

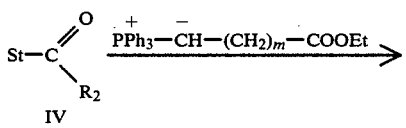

-continued
SCHEME II

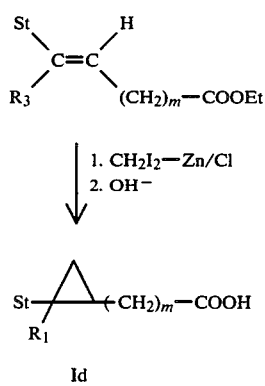

SCHEME III

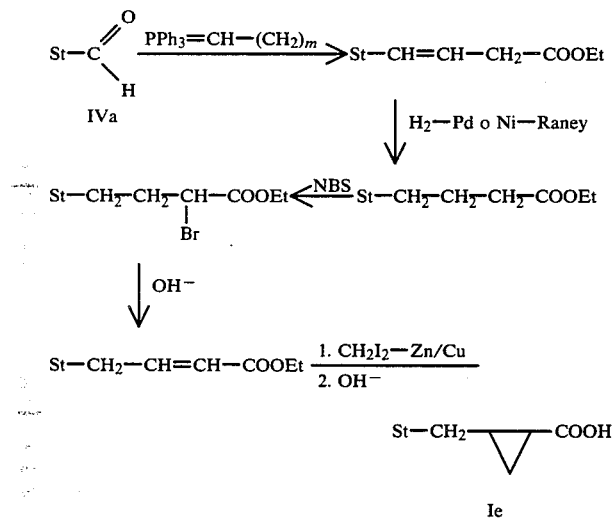

In the II and III schemes the compounds (IV), known because deriving from the degradation of the side chain of natural products, are subjected to a Wittig reaction with phosphorus ylides obtained for instance from triphenylphosphine and α or β-haloesters, according to known methods.

The so obtained olephinic compound can also be directly treated with $CH_2I_2$ (Scheme II) in the reaction conditions according to Simmons-Smith (J. Am. Chem. Soc. 80, 5323, 1958 and Org. Reactions 20, 1, 1973) and subsequently hydrolyzed to acid or (Scheme III), when the compounds wherein n=1 and R=H are to be prepared, the olephinic compound can be hydrogenated, halogenated in the position α to the carboxylic group with N-bromosuccinimide, dehydrohalogenated by means of alcohols and lastly the isomeric olephine obtained is subjected to Simmons-Smith reaction and final hydrolysis to compounds of general formula Ia, with conditions and synthesis methods per se known.

Of course many modifications can be carried out on the above exemplified schemes, without departing however from the scope of the invention: for instance different protective groups of the hydroxy groups of the St nucleus may be used, different solvents and reagents can also be used as well as phase-transfer catalysis techniques.

It is also plain that the products obtained from the above described processes can be present in numerous isomeric forms from the steric point of view.

The invention refers of course to all the possible stereoisomers of the claimed compounds.

The following examples further illustrate the process of the invention, without limiting in any way the scope thereof.

EXAMPLE 1

(a) 3α,7β-Diacetoxy-$\Delta^{22}$-24-norcholene (IIIa)

A mixture of ursodeoxycholic acid (40 g), acetic anhydride (60 ml), and pyridine (48 ml) was left to react overnight. The reaction mixture was poured on icewater and extracted with chloroform. The organic phase was washed with 10% HCl to acidity, then with water to neutrality, dried on $MgSO_4$ and evaporated. The crude product so obtained, without further purification, $Pb(OAc)_4$ (70 g), $Cu(OAc)_2$ (4 g), pyridine (10 ml), dissolved in anhydrous benzene (2 l), were refluxed under stirring in nitrogen atmosphere for 4 hours. After cooling, the reaction mixture was treated with ethylene glycol (2×200 ml), diluted with ether (1 l), washed with 10% KOH (3×150 ml), washed with water to neutrality, dried on $Na_2SO_4$ and evaporated.

After column chromatography ($SiO_2$; h=30 cm, φ=4.3 cm; petroleum ether/ethylether 96/4) 8.5 g of IIIa (m.p. 112°-114° C.) were obtained.

(b) Ethylester of 3α,7β-diacetoxy-22,23-methanate-ursodeoxycholic acid

A solution of ethyl diazoacetate (EDA) (3.1 ml, 0.03 mol) in cyclohexane (80 ml), was added, with very slow dripping (2 days), to a suspension of IIIa (8.5 g, 0.02 mol), Cu-Bronze ($\approx$10 g), in anhydrous cyclohexane (170 ml), refluxed under stirring in nitrogen atmosphere.

The reaction mixture after cooling was filtered and evaporated.

The residue was subjected to column chromatography ($SiO_2$; h=35 cm; φ=3 cm).

By eluting with petroleum ether containing 2% of ethylether, and increasing the percentage of ethylether by 1% every 200 ml of eluent until reaching the 7%, there were obtained: a fraction containing V (4.7 g), an α fraction (0.55 g), and α+β fraction (0.9 g), and a β fraction (1.8 g). The NMR spectrum of the α and β fractons is in agreement with the compound structure.

(c) 22,23-Methanate-ursodeoxycholic acid

A solution of the β chromatographic fraction (1.8 g) in 15% NaOH in $ETOH/H_2O$ (6:4, 180 ml) was kept at reflux under stirring for 4 h. After cooling, the reaction mixture was diluted with $H_2O$, acidified with conc. HCl, and extracted with chloroform. The organic phase was dried on $Na_2SO_4$ and evaporated. By column chromatography ($SiO_2$; h=35 cm; φ=2.1 cm) and eluting with chloroform a substance C (240 mg) (m.p. 133°-136° C.) was obtained; going by to elute with chloroform with 2% of methanol a substance D (270 mg) (m.p. 153°-159° C.) in addition to the mixture of the two C+D (370 mg) was obtained. The chemico-physical properties of C and D are in agreement with the compound structure. Similarly, by hydrolysis of the α fraction two substances A (m.p. 242°-244° C.) and B (m.p. 252°–255° C.) were obtained; the structure of 22,23-methanate-ursodesoxycholic acid can be proposed also for them.

(d) Sodium tauro-3α,7β-dihydroxy-22,23-methanate-5β-cholanate

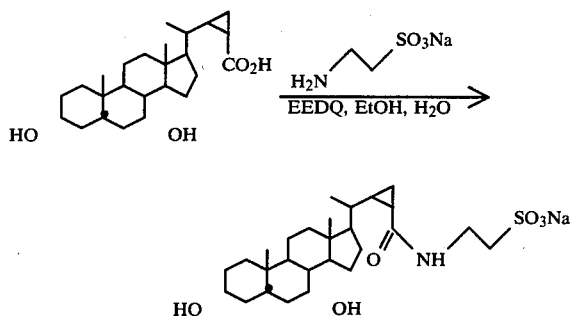

N-Ethoxycarbonyl-2-ethoxy-1,2-dihydroquinoline (EEDQ) (1.34 g, 5.40 mmol.) dissolved in 95% ethanol (55 ml) and taurine (0.483 g, 3.86 mmol) dissolved in sodium hydroxide N/2 (7.7 ml) were added to a solution of 3α,7β-dihydroxy-22,23-methanate-5β-cholanic acid (1.56 g, 3.86 mmol.) in 95% ethanol (80 ml). The reaction mixture was kept under stirring at the temperature of 40° C. After 18h the solvent was evaporated under vacuum at the temperature of 38° C. and the residue was dissolved in methanol (27 ml). A crystalline suspension, which was centrifuged, was obtained by addition of ethyl ether (100 ml); the surnatant was decanted and the precipitate was dissolved three times in methanol (20 ml), precipitated again with ether (100 ml) and centrifuged. The residue so obtained was dryed at 120° C. (1 mmHg) for 12 h to give 1.4 g (70%) of sodium 22,23-methanate-tauroursodesoxycholic. M.p. 113°–118° C.

EXAMPLE 2

(a) 3α,7β-diacetyl-20-methylene-5β-pregnane 1.95 g of carbonyldiimidazole were added to a solution of 4.5 g of diacetyl-ursodeoxycholic acid in 50 ml of anhydrous tetrahydrofuran. The reaction mixture was magnetically stirred in nitrogen atmosphere for 3 hours.

450 ml of tetrahydrofuran were then added and the mixture was irradiated for 16 hours with a low-pressure mercury vapor lamp.

The solvent was evaporated under vacuo and the residue was chromatographed on a silica column obtaining 910 mg of pure olephine. Melting point: 80°–90° C.

(b) 3α,7β-Dihydroxy-20,22-methylene-5β-cholan-23-oic acid 49 ml of dichloromethane and 36 mg of rhodium acetate were added to 1.9 g of 3α,7β-diacetyl-20-methylene-5β-pregnane: the reaction mixture was refluxed under nitrogen stream and 1 g of ethyl diazoacetate dissolved in 30 ml of methylene chloride was added at a rate of 0.44 ml per hour. The solvent was then evaporated and the residue chromatographed on a silica column. By elution with petroleum ether/ethyl ether 6:4, 2.21 g (95% yield) of the ethyl ester of 3α,7β-diacetyl-20,22-methylene-5 β-cholan-23-oic were obtained.

2.3 g of the diacetyl cyclopropane ester were dissolved in a sodium hydroxide hydroalcoholic solution (ethyl alcohol 51 ml, $H_2O$ 30 ml, sodium hydroxide 12 g).

The mixture was refluxed for 3 hours, acidified with conc. hydrochloric acid and extracted at last with ethyl acetate (3×50 ml). The organic phases were collected, washed with a saturated NaCl solution, dried on $MgSO_4$ obtaining, after evaporation under vacuum, 1.5 g of the 3α,7β-dihydroxy-20,22-methylene-5β-cholan-23-oic acid, yield 88%, melting point 125°/140° C.

The $[\alpha]_D$, pKa, the retention factor and the critical micellar concentrations (CMC), important because related to the capacity to form micelles in the bile and function of the hydrophilic/lipophilic balance, have been determined on the A, B, C, D isomers of 22,23-methanate-ursodeoxycholic acid. The CMCs have been measured by the method of the solubilization of insoluble dyes such as Azulene and Orange OT (Roda et al., J. Biol. Chem., in press).

The results are reported in Table I, in comparison with ursodeoxycholic acid.

TABLE I

| Bile acids | $[\alpha]_D^{25}$ | pKa* (SD = 0.01) | $H_2O$ CMC mM | $Na^+$ 0.15 M CMC mM | K'** μM |
|---|---|---|---|---|---|
| Isom. A | +56.4 ± 0.4 c = 1.1 EtOH | 5.03 | 25 | 16 | 0.21 |
| Isom. B | +7.5 ± 0.8 c = 2.7 EtOH | 5.06 | 20 | 12 | 0.80 |
| Isom. C | +14.5 ± 0.4 c = 1.3 EtOH | 5.02 | 14 | 8 | 1.30 |
| Isom. D | +59.9 ± 0.4 c = 1.1 EtOH | 5.04 | 10 | 6 | 2.05 |
| Ursodex | +57 c = 2 EtOH | 5.06 | 19 | 11 | 0.95 |

*Determined by potentiometric titration.
**K' = Retention factor. It has been calculated from the retention times on HPLC using as stationary phase a C-18 column and as mobile phase a mixture of methanol/-$H_2O$ 130/70; pH 5.7.

The biological properties of 22,23-methanate-ursodeoxycholic acid (CUDCA) were determined in comparison with ursodeoxycholic acid (UDCA) studying the hepatic uptake in isolated rat livers according to the method of Mortimore (Am. J. Physiol. 1961, 200, 1315) and the bile lipid secretion in anaesthetized Sprague-Dawley rats (300–330 g) treated i.v. with 50 mg of the compounds under study and collecting the bile at 15 min. intervals for 5 h, measuring the bile volume and the phospholipid, cholesterol and bile acids (BA) concentrations.

The results, reported in Table 2, show that the uptake of the compound of the invention, as well as the interaction with human serum albumina (HSP), is efficient and comparable to that exhibited by UDCA.

As far as bile lipid secretion is concerned, the compound of the invention inhibited the cholesterol secretion and stiumlated both the bile flow and the bile lipid secretion.

The structure of the rat livers was also evaluated by light microscopy at the end of the study, and the intravenous injection of 50 mg of CUDCA did not alter the basic morphology of the liver.

These results indicate the therapeutic value of compounds I as cholesterol-dissolving drugs.

TABLE II

Biological properties of 3α, 7β-dihydroxy-22,23-methylene-5β-cholan-24-oic acid (CUDCA) and 3α, 7β-dihydroxy-5α-cholan-24-oic acid*.

| | CUDCA | UDCA | CONTROLS |
|---|---|---|---|
| Hepatic uptake, % | 46 ± 1 | 50 ± 2 | |
| Albumin affinity constant × $10^4$ L/mol | 6.8 ± 0.4** | 3.8 ± 0.2 | |
| Bile flow, ml/h | 1.68 ± 0.20*** | 1.08 ± 0.15*** | 0.55 ± 0.12 |
| BA secretion, μmol $kg^{-1} h^{-1}$ | 97 ± 9 | 98 ± 7 | 61 ± 8 |
| Cholesterol secretion, μmol $kg^{-1} h^{-1}$ | 2.70 ± 0.14*** | 2.12 ± 0.09*** | 1.66 ± 0.12 |
| Phospholipid secretion, mol $kg^{-1} h^{-}$ | 9.50 ± 0.44*** | 6.47 ± 0.54 | 6.92 ± 0.44 |

*The control values were obtained on five rats studied under similar conditions to the BA treated rats. Each value represents the mean plus or minus the SD of five determinations.
**p < 0.01 vs. UDCA.
***p < 0.01 vs. controls.

The present invention refers also to all the industrially applicable aspects connected with the therapeutic use of the compounds of the invention. An essential aspect of the invention is therefore provided by pharmaceutical compositions suitable for the oral, parenteral administration containing as the active principle at least a compound of formula I, optionally in admixture with the excipients of conventional use in pharmaceutical technique. Examples of such composition comprise capsules, tablets, sugar coated tablets, sachets, solutions, injection vials, containing from 10 to 250 mg of compounds I. Said compositions may be administered 2-3 times a day.

We claim:

1. Compounds of general formula I

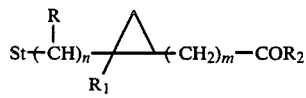

wherein: St represents the 17-ethiocholanyl residue, having two or more hydroxy groups both in the α and β conformation, some of which being optionally replaced by keto groups;

n is zero or 1:

R and $R^1$ represent hydrogen or methyl, with the proviso that when one of them is methyl the other one is hydrogen;

m is zero, 1 or 2;

$R^2$ represents OH or taurine or glycine residues, optionally salified, of formula $-NH(CH_2)_2SO_3H$ and $NHCH_2COOH$;

with the proviso that when N is 1, m is zero and, when n is 1 and R is methyl, $R_2$ is different from OH.

2. Compounds according to claim 1 wherein St is 3α,7β,12α-trihydroxy-17-ethiocholanyl residue.

3. Compounds according to claim 1 wherein St is 3α,7α,12α-trihydroxy-17-ethiocholanyl residue.

4. Compounds according to claim 1 wherein St is 3α,7β-dihydroxy-17-ethiocholanyl residue.

5. Compounds according to claim 1 wherein St is 3α,7α-dihydroxy-17-ethiocholanyl residue.

6. Compounds according to claim 1, wherein n is 1, R is methyl and $R_2$ is an optionally salified glycine or taurine residue.

7. Compounds according to claim 1, wherein n and m are zero and $R^1$ is methyl.

8. Compounds according to claim 1, wherein n is 1, R and $R^1$ are hydrogen.

9. Compounds according to claim 1, wherein n and m are zero and R and $R^1$ are hydrogen.

10. Compounds according to claim 1, wherein n is zero, $R^1$ is hydrogen or methyl and m is 1 or 2.

11. Process for the preparation of taurine or glycine conjugated of the compounds of claim 1 ($R^2$ different from OH) characterized in that the corresponding acids are reacted with glycine or taurine, in the presence of sodium hydroxide and N-ethoxy-carbonyl-2-ethoxyl-1,2-dihydroquinoline, in alcoholic or hydroalcoholic solution.

12. Process for the preparation of compounds of the claim 1, wherein m is zero characterized in that olephinic intermediates having formula

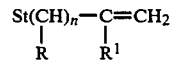

wherein n, R, $R_1$ and St have the above mentioned meanings are reacted with alkyl diazoacetate in the presence of Cu-bronze or rhodium acetate and of inert solvents.

13. Process according to claim 12 characterized by operating in anhydrous cyclohexane, at the reflux temperature and in inert atmosphere.

14. Process for the preparation of compounds of the claim 1 wherein m is 1 or 2 and n is zero characterized in that compounds of formula

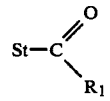

are subjected to Wittig reactions with suitable phosphorous ylides of alkyl esters and that the intermediates of formula

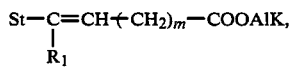

wherein $R_1$, St and m have the above mentioned meanings, are reacted with $CH_2I_2$ and Zn/Cu according to Simmons-Smith in inert solvents such as diethyl ether, tetrahydrofuran or 1,2-dimethoxyethane.

15. Pharmaceutical compositions characterized by containing as the active ingredient one or more compounds of claim 1.

* * * * *